United States Patent [19]
Orsat et al.

[11] Patent Number: 5,902,738
[45] Date of Patent: *May 11, 1999

[54] ENZYMATIC ACYLATION

[75] Inventors: Bernard Orsat, Allschwil; Paul Spurr, Riehen; Beat Wirz, Reinach, all of Switzerland

[73] Assignee: Roche Vitamins Inc., Parsippany, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/829,280

[22] Filed: Mar. 31, 1997

[30] Foreign Application Priority Data

Apr. 18, 1996 [EP] European Pat. Off. .............. 96106086
Feb. 20, 1997 [EP] European Pat. Off. .............. 97102768

[51] Int. Cl.$^6$ .............................. C12P 7/02; C12N 11/02; C12N 9/20; C07C 67/02
[52] U.S. Cl. ........................ 435/155; 435/198; 435/177; 560/260
[58] Field of Search .................................... 435/155, 198, 435/177, 178; 552/653; 560/260

[56] References Cited

PUBLICATIONS

Kwo–Feng Hsiao, et al. Biotechnology Letters vol. 18, No. 11 (Nov. 1996) pp. 1277–1282.
Cesti et al. *Appl. Biochem.Biotechnol.*, 11:401–407 (1985).
Rees et al. *Ind. J. Chem.*, 32:30–34 (1993).
Miyao et al. *J. Chem. Soc.*, Chem. Commun., 1535–1536 (1989).
Ottolina et al. *J. Org. Chem.*, 55:2366–2369 (1990).
Akita et al. *Tetrahedron: Asymmetry*, 4:757–760 (1993).
Ramaswamy et al. *Tetrahedron Letters.*, 31:3405–3408 (1990).
Cañada et al. *Biochemistry*, 29(41):9690–9697 (1990).
O'Connor et al. *Journal of Lipid Research*, 29(12):1693–1697 (1988).
Lazar et al. "Synthesis of esters by lipase" In: "World Conference of Emerging Technology" (1985) pp. 346–354.
Deryabina et al. "Synthesis of retinoids. Communication 2. Acetylation of dioline C20 and diol C20", Khim.–Farm. Zh. (1992) 26(5): 79–81 (abstracts only).

O'Conner et al. "*Candida cylindracea* lipase–catalyzed synthesis of retinyl and oleyl palmitates; Carbon chain length dependence of esterase activity", Aust. J. Chem. (1992) 45: 641–649.

Takahashi et al. "Lipase made active in hydrophobic media", J. Am Oil Chem. Soc. (Jun. 1988) 65(6): 911–916.

Barry et al. "Solubilization and partial purification of retyl ester synthase ad retinoid isomerase from bovine ocular pigment epithelium", J. Biol. Chem. (Jun. 1989) 264(16): 9231–8.

*Primary Examiner*—Jon P. Weber
*Assistant Examiner*—Susan Hanley
*Attorney, Agent, or Firm*—George W. Johnston; Dennis P. Tramaloni

[57] ABSTRACT

A process for making a compound of formula

I

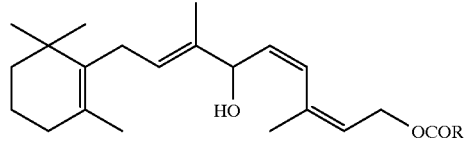

wherein R signifies a $C_{1-23}$-alkyl group or a $C_{2-23}$-alkenyl group containing 1 to 3 double bonds, comprising the steps of (a) reacting a compound of formula

II

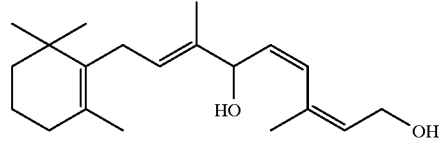

with an acylating agent which is in a mixture comprising (i) an organic solvent and (ii) a lipase which is present in suspension, so as to form the compound of formula I; and (b) recovering the compound of formula I is provided for. The process can be used to make (11Z,13Z)-7,10-dihydro-10-hydroxy-retinyl acetate, an starting material for the production of vitamin A acetate.

37 Claims, 5 Drawing Sheets

Figure I

ENZYMATIC ACYLATION

BACKGROUND OF THE INVENTION

The present invention is concerned with a novel process for making a compound of formula

I

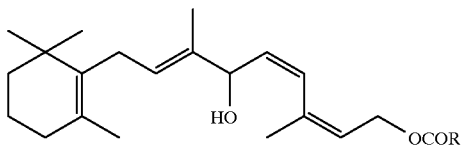

wherein R signifies a $C_{1-23}$-alkyl group or a $C_{2-23}$-alkenyl group (as defined in more detail hereinafter), by the enzyme-catalyzed, selective monoacylation of a compound of formula

II

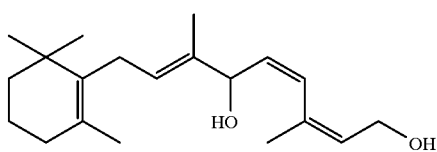

The compounds of formula I, (11Z,13Z)-7,10-dihydro-10-hydroxy-retinyl acylates [(2Z,4Z,7E)-carboxylic acid 3,7-dimethyl-6-hydroxy-9-[2',2',6'-trimethyl-cyclohex-6'-en-1'-yl]nona-2,4,7-trienyl esters], are starting materials used for making the corresponding vitamin A acylates, namely by cleavage of water and simultaneous cis-trans isomerization, which can be carried out in a manner known per se. Using the usual standard esterification methods there is obtained, for example, by acetylating the compound of formula II [(11Z,13Z)-7,10-dihydro-10-hydroxy-retinol, otherwise named (2Z,4Z,7E)-3,7-dimethyl-9-[2',2',6'-trimethyl-cyclohex-6'-en-1'-yl]nona-2,4,7-trien-1,6-diol] in addition to the desired and especially important compound of formula I wherein R is methyl, i.e. (11Z,13Z)-7,10-dihydro-10-hydroxy-retinyl acetate, also the byproduct compound (11Z,13Z)-7,10-dihydro-10-acetoxy-retinyl acetate [(2Z,4Z,7E)-acetic acid 6-acetoxy-3,7-dimethyl-9-[2',2',6'-trimethyl-cyclohex-6'-en-1'-yl]nona-2,4,7-trienyl ester] of formula

III

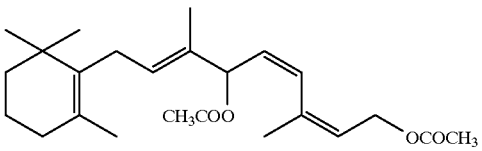

which occurs in varying amounts.

The (11Z,13Z)-7,10-dihydro-10-acetoxy-retinyl acetate of formula III is inert under the conditions of the catalytic dehydration and is therefore troublesome not only in the working-up of the compound of formula I, in which R signifies methyl [(11Z,13Z)-7,10-dihydro-10-hydroxy-retinyl acetate], but also in the working-up of vitamin A acetate. Accordingly, a process not only for the selective monoacetylation, but also generally for the selective monoacylation of a compound of formula II [(11Z,13Z)-7,10-dihydro-10-hydroxy-retinol] so as not to form diacylated byproducts, such as the compound of formula III, is of great interest.

An object of the present invention is to provide a process for making the compounds of formula I [(11Z,13Z)-7,10-dihydro-10-hydroxy-retinyl acylates] by the esterification of a compound of formula II [(11Z,13Z)-7,10-dihydro-10-hydroxy-retinol] which does not have the disadvantages of previously known procedures (e.g. undesired formation of the compound of formula III, (11Z,13Z)-7,10-dihydro-10-acetoxy-retinyl acetate. Thus, it is necessary that the process proceeds extremely selectively and in high yields, and that the material used to esterify the compound of formula II displays catalytic activity even in low amounts, can be readily separated and can be used again several times.

The selective acylation of primary hydroxy groups in addition to secondary in the presence of lipases is known from the literature. Thus, for example, according to J. Org. Chem. 55, 2366–2369 (1990) the acylation of amphenicols, i.e. of phenyl-substituted short-chain aliphatic diols, by esterification with a trifluoroethyl acylate or a cyclic anhydride is carried out using a lipase isolated from *Pseudomonas cyclopium*, with the yields being 83% and 64%, respectively, without the purity being given.

The racemate resolution of 2-methyl-5-(4-methoxyphenyl)pentane-1,3-diol by esterification with vinyl acetate in the presence of immobilized lipase PS is described in Tetrahedron: Asymmetry 4, 757–760 (1993), with the yield of monoacylated product being 66% and the optical purity being 42% e.e.

In Appl. Biochem. Biotechnol. 11, 401–407 (1985) a series of 1,2- and 1,3-diols (dissolved in ethyl acylates) has been acylated with lipase from porcine pancreas in yields of ≦97%.

According to J. Chem. Soc., Chem. Commun., 1989, 1535–1536, 2-ethyl-hexane-1,3-diol has been acylated with lipase from porcine pancreas in 60% yield.

Tetrahedron Lett. 31, 3405–3408 (1990) describes the selective acylation of aliphatic 1,n-diols with anhydrides in the presence of lipase from porcine pancreas, with the selectivities being ≦98% and the yields being ≦95%.

The selective acylation (98% selectivity) of 1,5-hexanediol with n-decanoic acid with lipase from *Chromobacterium viscosum* is described in Ind. J. Chem. 32, 30–34 (1993).

All of these previously known processes have certain disadvantages: thus all of these processes yield the desired products, but the selectivity and therewith the purity and/or the yield leave much to be desired. Moreover, none of these literature references mentions a repeated use of the lipase employed, i.e. the stability of the lipase, let alone a simultaneous substrate purification.

In the scope of the present invention the above-mentioned object of selective and high yield acylation with a material featuring high catalytic activity, ready separability and reuseability has been achieved by carrying out the acylation of the compound of formula II [(11Z,13Z)-7,10-dihydro-10-hydroxy-retinol] with an acylation agent in the presence of a lipase (enzyme class EC 3.1.1.3) to form the compound of formula I [an appropriate (11Z,13Z)-7,10-dihydro-10-hydroxy-retinyl acylate] under a variety of specific pre-reaction and reaction conditions.

SUMMARY OF THE INVENTION

The present invention is concerned with a process for making a compound of formula I,

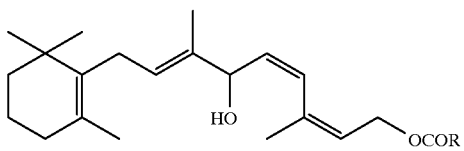

I where R signifies a $C_{1-23}$-alkyl group or a $C_{2-23}$-alkenyl group containing 1 to 3 double bonds, comprising the steps of (a) reacting a compound of formula II

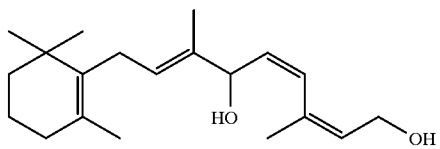

II with an acylating agent which is in a mixture comprising (i) an organic solvent and (ii) a lipase which is present in suspension, so as to form the compound of formula I; and (b) recovering the compound of formula I.

Suitable lipases for the purpose of the present invention are those of the enzyme class EC 3.1.1.3, which show good activity and selectivity, especially lipases selected from the group consisting of lipase PL from Alcaligenes sp., its immobilized forms lipase PLC and lipase PLG, and lipase MY-30 from *Candida cylindracea* (renamed *Candida rugosa*) (Meito Sangyo, Tokyo, Japan), Lipozyme® IM-20 from *Mucor miehei* (renamed *Rhizomucor miehei*) (Novo Nordisk, Bagsvaerd, Denmark; referred to hereinafter as lipase IM-20), lipase CE-5 from *Humicola lanuginosa*, lipase G from *Penicillium cyclopium* (both Amano Pharmaceutical Co. Ltd., Nagoya, Japan), and Chirazyme® L-2 from *Candida antarctica* (Boehringer Mannheim GmbH, Germany; formerly Novozym® SP 435 from Novo Nordisk; referred to hereinafter as lipase L-2). Lipase PL, lipase PLC, lipase PLG, lipase IM-20 (Lipozyme® IM-20) and lipase L-2 (Chirazyme® L-2) are especially preferred, with lipase PL, lipase PLC, lipase PLG and lipase L-2 (Chirazyme® L-2) being particularly preferred.

DETAILED DESCRIPTION OF THE INVENTION

Figure 1:
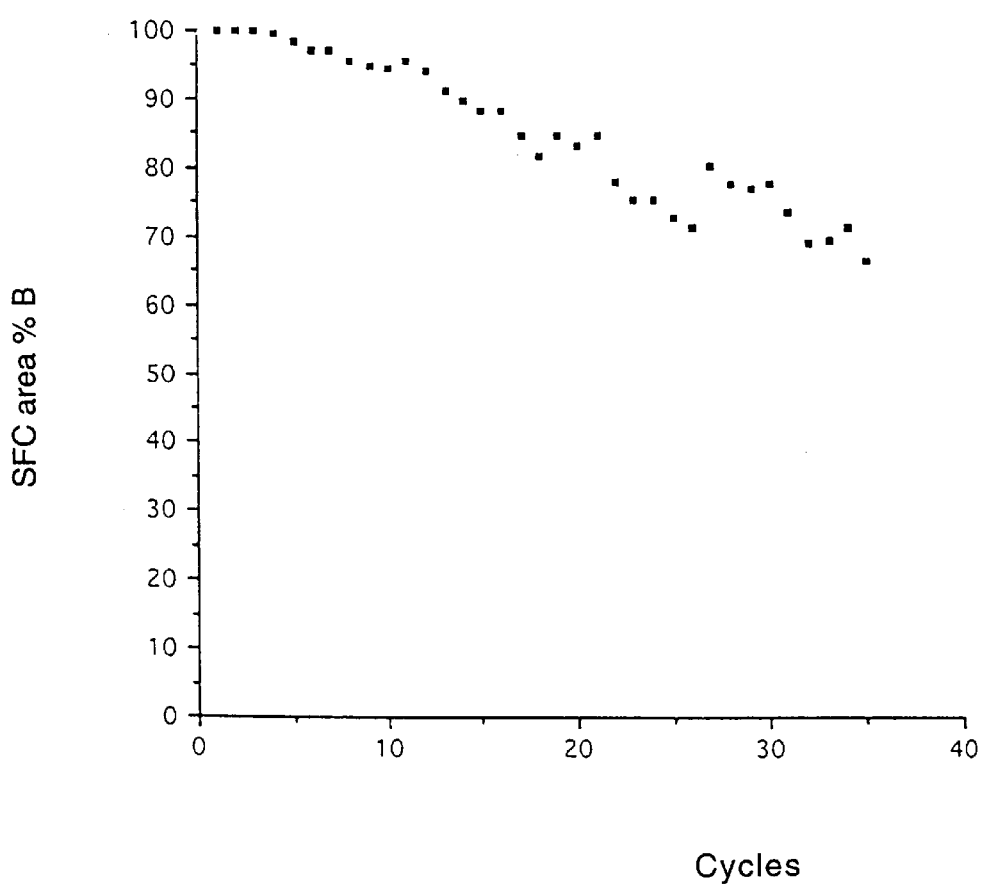
FIG. 1 shows the amount of B [(11Z,13Z)-7,10-dihydro-10-hydroxy-retinyl acetate] formed as provided for in Example 11.

The present invention is concerned with a process for making a compound of formula I,

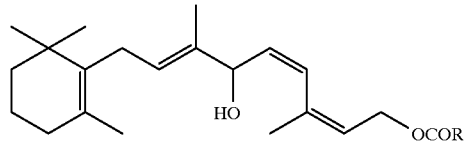

I wherein R signifies a $C_{1-23}$-alkyl group or a $C_{2-23}$-alkenyl group containing 1 to 3 double bonds, comprising the steps of (a) reacting a compound of formula II

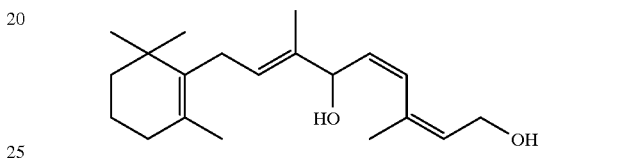

II with an acylating agent which is in a mixture comprising (i) an organic solvent and (ii) a lipase which is present in suspension, so as to form the compound of formula I; and (b) recovering the compound of formula I.

The acylation of the compound of formula II [(11Z,13Z)-7,10-dihydro-10-hydroxy-retinol] is carried out with an acylation agent as already mentioned in an organic solvent (which is preferably almost anhydrous) with a lipase which is present in suspension.

Suitable lipases for the purpose of the present invention are those of the enzyme class EC 3.1.1.3, which show good activity and selectivity, especially lipases selected from the group consisting of lipase PL from Alcaligenes sp., its immobilized forms lipase PLC and lipase PLG, and lipase MY-30 from *Candida cylindracea* (renamed *Candida rugosa*) (Meito Sangyo, Tokyo, Japan), Lipozyme® IM-20 from *Mucor miehei* (renamed *Rhizomucor miehei;* Novo Nordisk, Bagsvaerd, Denmark; referred to hereinafter as lipase IM-20), lipase CE-5 from *Humicola lanuginosa*, lipase G from *Penicillium cyclopium* (both Amano Pharmaceutical Co. Ltd., Nagoya, Japan), and Chirazyme® L-2 from *Candida antarctica* (Boehringer Mannheim GmbH, Germany; formerly Novozym® SP 435 from Novo Nordisk; referred to hereinafter as lipase L-2). Lipase PL, lipase PLC, lipase PLG, lipase IM-20 (Lipozyme® IM-20) and lipase L-2 (Chirazyme® L-2) are especially preferred, with lipase PL, lipase PLC, lipase PLG and lipase L-2 (Chirazyme® L-2) being particularly preferred.

Lipase L-2 (Chirazyme® L-2) is characterized by having an activity of 130 U/mg, measured as activity per mg lyophilisate determined with 5 mmol tributyrin in 50 ml of 10 mM $K_3PO_4$ at pH 7.0 and 25° C.; 1 Unit is the enzyme activity which liberates 1 μmol of butyric acid from tributyrin per minute. This enzyme has a stereoselectivity towards the hydrolysis of a chiral substrate (1-phenylethyl acetate) of (R) E>150, where (R) is the configuration of the hydrolysis product and E is the enantioselectivity value of the hydrolysis reaction.

Lipase IM-20 (Lipozyme® IM-20) is characterized by having an activity of ≧10 U/g dry form, determined with 150 mM tributyrin and 10 mM $K_3PO_4$ at pH 7 and 25° C., using an automatic burette. In the dry form it is a brown coloured granulate.

Under the term "$C_{1-23}$-alkyl group" or "$C_{2-23}$-alkenyl group containing 1 to 3 double bonds" (R of formula I) there are to be understood depending on the number of carbon atoms not only straight-chain, but also branched alkyl or alkenyl groups. Examples of $C_{1-23}$-alkyl groups are methyl, ethyl, propyl, pentyl, heptyl, undecyl, pentadecyl and heptadecyl, and examples of $C_{2-23}$-alkenyl groups are vinyl, allyl, isopropenyl, 8-heptadecenyl and heptadeca-8,11-dienyl. The corresponding alkanoyl and alkenoyl groups (RCO) are acetyl, propionyl, butyryl, caproyl, capryl, lauroyl, palmitoyl and stearoyl and, respectively, acryloyl, vinylacetyl, methacryloyl, oleoyl and linolyl. An especially preferred meaning for R is methyl, the process in accordance with the invention being in this case an enzyme-catalyzed, selective monoacetylation. If alkyl or alkenyl is used by itself herein, their respective meanings are equal to that of $C_{1-23}$-group or $C_{2-23}$-alkenyl group containing 1 to 3 double bonds.

In a batch process, the lipase, which is available as a powder, granulate or small beadlets, is used in up to 20 weight % (wt. %) (wt./wt. based on the compound of formula II, (11Z,13Z)-7,10-dihydro-10-hydroxy-retinol), but the amount of lipase preferably lies between about 0.1 wt. % and about 10 wt. %, particularly between about 1 wt. % and 5 wt. %, based on the compound of formula II.

Organic solvents which are suitable for the process of the present invention include aliphatic hydrocarbons of from 5 to 8 carbon atoms, such as hexane and heptane; alicyclic hydrocarbons of from 6 to 10 carbon atoms, such as cyclohexane, methylcyclohexane and decalin; chlorinated aliphatic hydrocarbons, such as methylene chloride, chloroform and carbon tetrachloride; nitro-substituted aliphatic hydrocarbons, such as nitromethane; aromatic hydrocarbons, such as toluene and xylene; aliphatic ethers, such as 1,2-dimethoxyethane, diethyl ether, diisopropyl ether and tert.butyl methyl ether; cyclic ethers, such as tetrahydrofuran, methylfuran and 1,4-dioxan; aliphatic esters, such as trimethyl orthoformate, ethyl acetate, butyl acetate, vinyl acetate, vinyl propionate and isopropenyl acetate; aliphatic ketones, such as acetone; aliphatic nitriles, such as acetonitrile; aliphatic amines, such as triethylamine; aliphatic acetals, such as formaldehyde dimethyl acetal; and mixtures of such solvents. Preferred organic solvents are hexane, cyclohexane, methylene chloride, carbon tetrachloride, toluene, diisopropyl ether, vinyl acetate, vinyl propionate, tetrahydrofuran, methylfuran, formaldehyde dimethyl acetal, and mixtures formed therefrom, and especially preferred organic solvents are methylene chloride, diisopropyl ether, vinyl acetate, vinyl propionate, tetrahydrofuran, formaldehyde dimethyl acetal and mixtures formed therefrom.

A variety of conventional alkyl acylates and alkenyl acylates, such as methyl acetate, ethyl acetate, butyl acetate, vinyl acetate, allyl acetate, isopropenyl acetate, ethyl propionate, ethyl butyrate and vinyl propionate as well as esters of long-chain fatty acids, e.g. vinyl laurate, can be used as the acylating agent. Preferably, ethyl acetate, butyl acetate or vinyl acetate, particularly vinyl acetate, is used for the acylation. Vinyl propionate is preferred for the manufacture of the propionate (R=ethyl), and the vinyl esters of the corresponding fatty acids are also preferred for the manufacture of long-chain acylates. The amount of acylating agent used can lie between 1 molar equivalent and a several times greater excess; the acylating agent is used in excess especially when it simultaneously serves as the solvent, which can be the case with alkyl and alkenyl acylates.

The concentration of the compound of formula I is conveniently from about 10% to about 50%, preferably from about 20% to about 45%, and more preferably from about 20% to about 40% [expressed in weight/volume (wt./vol.)]. The solubility of the educt is controlled by the choice of solvent or solvent mixture and/or the temperature. Thus, the reaction temperature advantageously lies between from about 10° C. to about the reflux temperature of the reaction mixture, preferably between from about room temperature (about 20° C.) to about 90° C., and especially preferred between from about room temperature (about 20° C.) to about 60° C. In the batch process, the compound of formula I need not be in solution at the start of the reaction; rather a suspension can also be present at the start of the reaction.

In order to improve the accessibility to the lipase and its re-use, it can be immobilized on various carrier materials. This immobilization can be effected covalently or non-covalently, preferably non-covalently, by simple adsorption on a suitable carrier material having a large surface. Since lipase and carrier material are insoluble in organic solvents, no measurable desorption takes place during the reaction. Suitable carrier materials are many of the usual, inexpensive filter aids, adsorbents, ion exchangers and chromatography materials, such as Florisil®, diatomaceous earth, bentonite, cellulose, molecular sieve, Amberlite®, Amberlyst®, silica gel or aluminum oxide and the like, as well as other inexpensive materials having large surface areas, such as sand, sintered glass or hollow fibres and the like. The use of diatomaceous earth and sea sand is preferred. Alternatively, commercially available, already immobilized lipase preparations can also be used, for example the lipase preparations from Meito Sangyo and Boehringer Mannheim GmbH:

Lipase PLC: Lipase PL immobilized on diatomaceous earth;

Lipase PLG: Lipase PL immobilized on granulated diatomaceous earth.

Lipase L-2 (Chirazyme® L-2, formerly Novozym® SP 435): lipase from *Candida antarctica*, immobilized on macroporous polyacryl.

If desired, the immobilization of the lipase can also be effected in the presence of a "cholanic salt" (co-immobilization), by means of which the activity can in part be controlled (activator). Suitable cholanic salts are e.g. sodium cholate and sodium deoxycholate.

In order to exclude the danger of chemical side-reactions practically from the outset, the reaction with the lipase is conveniently carried out under an inert gas atmosphere, e.g. nitrogen or argon, and with the exclusion of light and/or in the presence of a radical scavenger, e.g. hydroquinone or (2,6-di(tert.butyl))-p-cresol.

In the batch process the catalyst can be filtered off after one run and re-used. The water content of the reaction solution—and thus of the lipase—inter alia plays a role with respect to the stability and activity of the lipase. The addition of a small amount of water (<0.2% of the reaction solution) has a positive influence on the lipase activity; weak basic solutions, such as ammonium bicarbonate or ammonium hydroxide solutions, or organic bases, e.g. triethylamine or ethyidiisopropylamine, have an even better effect. The addition of the water can also be effected periodically or in the sense of an equilibration step.

For the efficient re-use of the lipase, which is extremely important for the economy of the process, the purity of the educt is also decisive: the long-term stability of the lipase preparation can be improved considerably by an appropriate purification of the educt, which from the earlier stage still contains, inter alia, heavy metals. Filtration over various aids, such as diatomaceous earth, silica gel, ethylenediaminetetraacetic acid (EDTA) salts and aluminum oxide, and washing with aqueous EDTA solution having a pH value of about 8 have been found to be simple and effective purification procedures, with the aid of which, inter alia, the heavy metal content of the educt can be lowered and the efficacy of the lipase preparation improved.

The process in accordance with the invention can be carried out as a repeated batch process or as a continuous process, namely using conventional types of reactor, such as, for example, a solid bed reactor, cylinder reactor, filament reactor, rotary reactor, fluidized bed reactor (with a false bottom) or slurry reactor.

The aforementioned use of a compound of formula I, e.g. the compound where R is methyl [(11Z,13Z)-7,10-dihydro-10-hydroxy-retinyl acylate, e.g. the acetate], obtained in accordance with the invention, for making the corresponding vitamin A acylate or, respectively, of vitamin A acetate, represents a further aspect of the present invention.

The following Examples for making various compounds of formula I [(11Z,13Z)-7,10-dihydro-10-hydroxy-retinyl acylates] by reacting the compound of formula II ((11Z,13Z)-7,10-dihydro-10-hydroxy-retinol) with an acylating agent in a mixture of organic solvent and a lipase which is in suspension illustrate advantageous embodiments of the process in accordance with the invention, but do not in any manner represent a limitation. All temperatures are given in degrees Celsius.

EXAMPLE 1

10.0 g (32.8 mmol) of (11Z,13Z)-7,10-dihydro-10-hydroxy-retinol and 10 mg of 2,6-di(tert.butyl)-p-cresol (BHT) were dissolved in a mixture of 30 ml of toluene and 5 ml of vinyl acetate (54.1 mmol). The reaction was started by the addition of 500 mg of lipase PLC (Meito Sangyo) and the suspension was stirred gently at room temperature for 17 hours on a roller. The lipase was thereafter filtered off and washed with toluene, and the filtrate was evaporated. After drying under a high vacuum for one day there were obtained 11.4 g (33 mmol) of (11Z,13Z)-7,10-dihydro-10-hydroxy-retinyl acetate in a yield of 100.6% and a purity of >99% [according to supercritical fluid chromatography (SFC) area percent].

EXAMPLE 2

10.0 g (32.8 mmol) of (11Z,13Z)-7,10-dihydro-10-hydroxy-retinol were taken up in a mixture of 6.8 ml of toluene and 3.2 ml (34.6 mmol) of vinyl acetate. The reaction was started by the addition of 500 mg of lipase PLC (Meito Sangyo) and the reaction mixture was stirred gently at room temperature for 16 hours. The lipase was thereafter filtered off and washed with toluene, and the filtrate was concentrated by evaporation. After drying under a high vacuum and stirring for one day there were obtained 11.23 (32.4 mmol) of (11Z,13Z)-7,10-dihydro-10-hydroxy-retinyl acetate in a yield of 98.8% and a purity of 97.2% (SFC area percent).

EXAMPLE 3

20.0 g (65.7 mmol) of (11Z,13Z)-7,10-dihydro-10-hydroxy-retinol and 20 mg of BHT were dissolved in 56 ml of toluene, 56 ml of tert.butyl methyl ether (TBME) and 7.5 ml (81.2 mmol) of vinyl acetate. The reaction was started by the addition of 1.0 g of lipase PLC (Meito Sangyo) and the suspension was stirred gently at 40° for 16 hours. The lipase was thereafter filtered off and washed with toluene, and the filtrate was evaporated. After drying under a high vacuum for one day there were obtained 23.1 g (66.7 mmol) of (11Z,13Z)-7,10-dihydro-10-hydroxy-retinyl acetate in a yield of 101.5% and a purity of >99% (SFC area percent).

EXAMPLE 4

(A) Immobilization on various carrier materials: 2.0 ml of lipase PL solution (25 mg/ml bidistilled water) were added to 2.5 ml of carrier material and the suspension obtained was stirred carefully at room temperature. The similarly wetted carrier was dried by gradually and cautiously increasing the vacuum (foam formation). Finally, the carrier was dried in a high vacuum for 2 days and used as described hereinafter.

(B) Immobilization on porous glass beads: 2.0 ml of lipase PL solution (20 mg/ml bidistilled water) were added to 2.0 g of Siran Carrier Sikug 041/02/120/A (porous, sintered glass from Schott Glaswerke, Mainz, Germany) and the suspension was dried as described above under (A).

8.0 ml aliquots of a 2:2:1 mixture of hexane, tert.butyl methyl ether (TBME) and vinyl acetate containing 1.0 g of (11Z,13Z)-7,10-dihydro-10-hydroxy-retinol were added to the dried lipase preparations obtained as described above and the reaction solution was stirred gently at room temperature on a roller. 25 µl samples were removed after 6 hours and 27 hours for HPLC analysis. The results are shown in Table 1 where A stands for (11Z,13Z)-7,10-dihydro-10-hydroxy-retinol and B stands for (11Z,13Z)-7,10-dihydro-10-hydroxy-retinyl acetate.

TABLE 1

| | | HPLC area percent | | | |
| | | A | | B | |
| # | Carrier material | After 6 hrs. | 27 hrs. | After 6 hrs. | 27 hrs. |
|---|---|---|---|---|---|
| 1 | Silica gel 60 (0.2–0.5 mm; Merck) | | 38.2 | | 61.8 |
| 2 | Florisil ® | | 43.9 | | 56.1 |
| 3 | Sea sand (40–100 mesh; Fluka 84880) | 40.4 | 4.9 | 59.6 | 95.1 |
| 4 | Molecular sieve (3Å; Merck) | | 35.9 | | 64.1 |
| 5 | Avicel ® (microcrystalline cellulose) | | 29.0 | | 71.0 |
| 6 | DICALITE ® Speedex (diatomaceous earth) | 34.7 | 3.8 | 65.3 | 96.2 |
| 7 | Hyflo Super Cel ® (kieselgur; Fluka 56678) | | 36.8 | | 63.2 |
| 8 | Clarcel type Die/B (diatomaceous earth from CECA, Paris, France) | 41.1 | 6.5 | 58.9 | 93.5 |
| 9 | Bentonite (Fluka 11957) | | 74.8 | | 25.2 |
| 10 | Bentonite (Fluka 11959) | | 95.2 | | 4.8 |
| 11 | Aluminum oxide neutral I (Camag 507-C from Camag, Muttenz, Switzerland) | | 33.5 | | 66.5 |
| 12 | Aluminum oxide basic I (Camag 5016-A) | | 31.1 | | 68.9 |
| 13 | Amberlite ® XAD-7 (20–50 mesh) | | 33.1 | | 66.9 |

TABLE 1-continued

| | | HPLC area percent | | | |
| | | A | | B | |
| # | Carrier material | After 6 hrs. | 27 hrs. | After 6 hrs. | 27 hrs. |
|---|---|---|---|---|---|
| 14 | Amberlite ® XAD-8 (20–50 mesh) | | 46.2 | | 53.8 |
| 15 | Amberlyst ® A-21 (0.4–0.55 mm) | 38.0 | 12.6 | 62.0 | 87.4 |
| 16 | Amberlite ® IR-45 | | 21.9 | | 78.1 |
| 17 | Amberlite ® IRA-93 | 33.3 | 9.2 | 66.7 | 90.8 |
| 18 | Glass beads (0.5 mm) | | 70.1 | | 29.9 |
| 19 | Siran Carrier Sikug 041/02/120/A | | 34.1 | | 65.9 |

EXAMPLE 5

8.0 ml of a solution of 1.0 g of (11Z,13Z)-7,10-dihydro-10-hydroxy-retinol in a 2:2:1 mixture of hexane, TBME and vinyl acetate were treated with 30 mg of lipase PLC or 30 mg of lipase PLG and the suspension was stirred gently on a roller under argon at room temperature in the dark. After 24 hours the residual content of (11Z,13Z)-7,10-dihydro-10-hydroxy-retinol was less than 1% (HPLC). When 51 mg of lipase PLC or 51 mg of lipase PLG were used, (11Z, 13Z)-7,10-dihydro-10-hydroxy-retinol was no longer detectable after 24 hours.

EXAMPLE 6

25 mg of lipase PL and 0.5 mg of cholate salt (sodium cholate, sodium deoxycholate) were dissolved in 2.0 ml of bidistilled water and added to 2.5 g of DICALITE® Speedex or sea sand suspended in 6 ml of bidistilled water. The suspension was dried cautiously as in Example 4 and, when necessary, the dried material was pulverized.

The lipase preparations produced were tested with 8 ml of (11Z,13Z)-7,10-dihydro-10-hydroxy-retinol solution as described in Example 5. HPLC analysis was carried out after 24 hours in each case. The results are shown in Table 2 where A stands for (11Z,13Z)-7,10-dihydro-10-hydroxy-retinol.

TABLE 2

| Cholate salt | Carrier | Residual content of A (HPLC area %) |
|---|---|---|
| None | DICALITE ® | 9.1 |
| | Sea sand | 37.8 |
| Sodium cholate | DICALITE ® | 6.5 |
| | Sea sand | 31.2 |
| Sodium deoxycholate | DICALITE ® | 5.6 |
| | Sea sand | 32.3 |

EXAMPLE 7

50.0 g (164.2 mmol) of (11Z,13Z)-7,10-dihydro-10-hydroxy-retinol were dissolved in a mixture of 140 ml of hexane, 140 ml of TBME, 70 ml of vinyl acetate and 50 mg of BHT. 2.5 g of lipase PLC were added and the suspension was stirred gently on a roller at room temperature under argon and in the dark for 24 hours. Then, the lipase catalyst was filtered off, washed with diethyl ether and dried for re-use. The filtrate was then concentrated by evaporation together with the wash solution and thereafter concentrated by evaporation firstly with two 300 ml portions of hexane and then with 300 ml of pentane in order in this manner to remove azeotropically traces of acetic acid formed. After drying in a high vacuum at 35° for about 16 hours there were obtained 56.73 g (163.7 mmol, 99%) of (11Z,13Z)-7,10-dihydro-10-hydroxy-retinyl acetate as a pale yellowish oil.

Analysis: >99% purity (SFC area percent); confirmed by 250 -MHz-$^1$H-NMR (CDCl$_3$), El-MS (mle 346), IR (film) and microanalysis: Calc.: C 76.26%; H 9.89%; Found: C 76.07%; H 9.73%.

EXAMPLE 8

8.0 ml aliquots of a solution of 1.0 g of (11Z,13Z)-7,10-dihydro-10-hydroxy-retinol and 1 mg of BHT in a 2:2:1 mixture of hexane, TBME and vinyl acetate were each added to 50 mg of lipase PLC, which had already previously been used four times (as a single batch) under the same conditions and had been washed between the individual batches merely with a 1:1 mixture of hexane and TBME. Various aqueous solutions were then added to the individual samples, and the reaction suspensions were stirred gently on a roller for 17 hours and then analyzed by HPLC. The results are compiled in the Table 3 hereinafter in which B stands for (11Z,13Z)-7,10-dihydro-10-hydroxy-retinyl acetate.

TABLE 3

| Additive | B formed (HPLC area %) |
|---|---|
| None | 6 |
| 10 μl water | 19 |
| 10 μl 0.1M ammonium bicarbonate solution | 28 |

EXAMPLE 9

A. 1 kg of (11Z,13Z)-7,10-dihydro-10-hydroxy-retinol was dissolved in 8 l of ethyl acetate and washed at room temperature with two 3 l portions of a 50 mmolar EDTA solution having a pH value of 8.0. The organic phase was thereafter dried over anhydrous sodium sulphate and concentrated by evaporation, and the residue was dried in a high vacuum.

B. 50 ml aliquots of (11Z,13Z)-7,10-dihydro-10-hydroxy-retinol were dissolved in 400 ml of ethyl acetate and in each case filtered over 5 g of basic aluminum oxide, DICALITE Speedex® or silica gel. The filtrate was concentrated by evaporation and dried in a high vacuum.

C. 3.5 g of the (11Z,13Z)-7,10-dihydro-10-hydroxy-retinol samples purified according to A. or B. were dissolved in 25 ml of a 2:2:1 mixture of toluene, TBME and vinyl acetate. Three 8.0 ml samples were removed from each solution (triple experiment) and were each treated with 2.5 mg of lipase PLC. The reaction suspension was stirred gently on a roller at room temperature for 24 hours and subsequently analyzed by SFC. The results are shown in Table 4 where A and B stand for (11Z,13Z)-7,10-dihydro-10-hydroxy-retinol and (11Z,13Z)-7,10-dihydro-10-hydroxy-retinyl cetate, respectively.

TABLE 4

| Purification method | B formed (SFC area percent; minimal–maximal) | A + B (SFC area percent: Average) |
| --- | --- | --- |
| Not purified | 24.3–27.9 | 95.0 |
| EDTA | 73.2–77.8 | 99.4 |
| Aluminum oxide, basic | 69.0–70.4 | 99.6 |
| DICALITE ® Speedex | 68.4–73.4 | 99.7 |
| Silica gel | 51.7–55.2 | 99.7 |

EXAMPLE 10

5.0 g of lipase PLC were placed in a 2 l chromatography column having a glass frit. Then, 100.0 g of (11Z,13Z)-7,10-dihydro-10-hydroxy-retinol, 280 ml of hexane, 280 ml of TBME, 140 ml of vinyl acetate, which optionally contained 500 μl of a 0.1M ammonium bicarbonate solution or of a 1% ammonium hydroxide solution, and 100 mg of BHT were added in this sequence and the column was stirred gently by rotation (motorized stirrer), with the column having the outlet inclined upwards in order that the frit was not in contact with the solution. After incubation for 17 hours at room temperature the reaction solution was drained off and analyzed by SFC. The residual lipase preparation was washed firstly three times with 100 ml of a 1:1 mixture of hexane and TBME each time (for about 15 minutes per washing) and thereafter with 50 ml of hexane, and then again used for a new cycle. The results are shown in Table 5 where A and B stand for (11Z,13Z)-7,10-dihydro-10-hydroxy-retinol and (11Z,13Z)-7,10-dihydro-10-hydroxy-retinyl acetate, respectively.

TABLE 5

| | B formed (SFC area percent; A + B = 100%) | | | |
| --- | --- | --- | --- | --- |
| | 1st cycle | 2nd cycle | 3rd cycle | 4th cycle |
| A (not purified) | 99.0 | 92.0 | 50.6 | 22.7 |
| A + 0.1M NH₄HCO₃ per batch | 99.6 | 99.4 | 95.0 | 76.3 |
| A + 1%° NH₄OH per batch (Wash solution containing 1%° vol./vol. 1% NH₄OH) | 100 | 99.4 | 97.8 | 88.7 |
| A purified according to Example 9 A. | 100 | 100 | 100 | 99.8 |

EXAMPLE 11

(11Z,13Z)-7,10-Dihydro-10-hydroxy-retinol was purified as described in Example 9 A and thereafter used in a repeated batch process as described in Example 10, but using 3.0 g of lipase PLC, 90.0 g of (11Z,13Z)-7,10-dihydro-10-hydroxy-retinol, 250 ml of toluene, 250 ml of TBME and 125 ml of vinyl acetate, which contained 450 μl of 1% ammonium hydroxide solution. The reaction time was 23 hours. Between the cycles the lipase preparation was washed twice with 100 ml of a 1:1 mixture of toluene and TBME, which contained 1%o (vol./vol.) of a 1% ammonium hydroxide solution, and after every 4 cycles was left to stand for 3 days at room temperature in toluene. The results are shown in FIG. 1.

EXAMPLE 12

Figure 2:
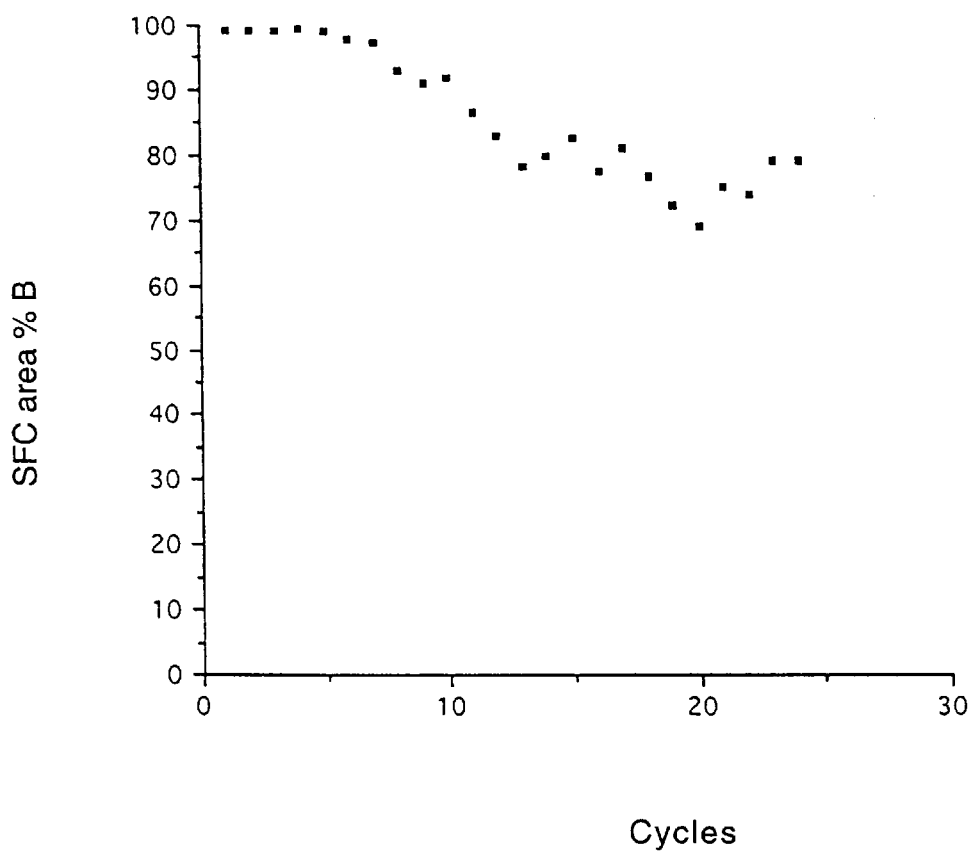
FIG. 2 shows the amount of B [(11Z,13Z)-7,10-dihydro-10-hydroxy-retinyl acetate] formed as provided for in Example 12.

The procedure was as described in Example 11, except that the (11Z,13Z)-7,10-dihydro-10-hydroxy-retinol was purified as described in Example 9 B. using DICALITE® Speedex. The results are shown in FIG. 2.

EXAMPLE 13

Figure 3:
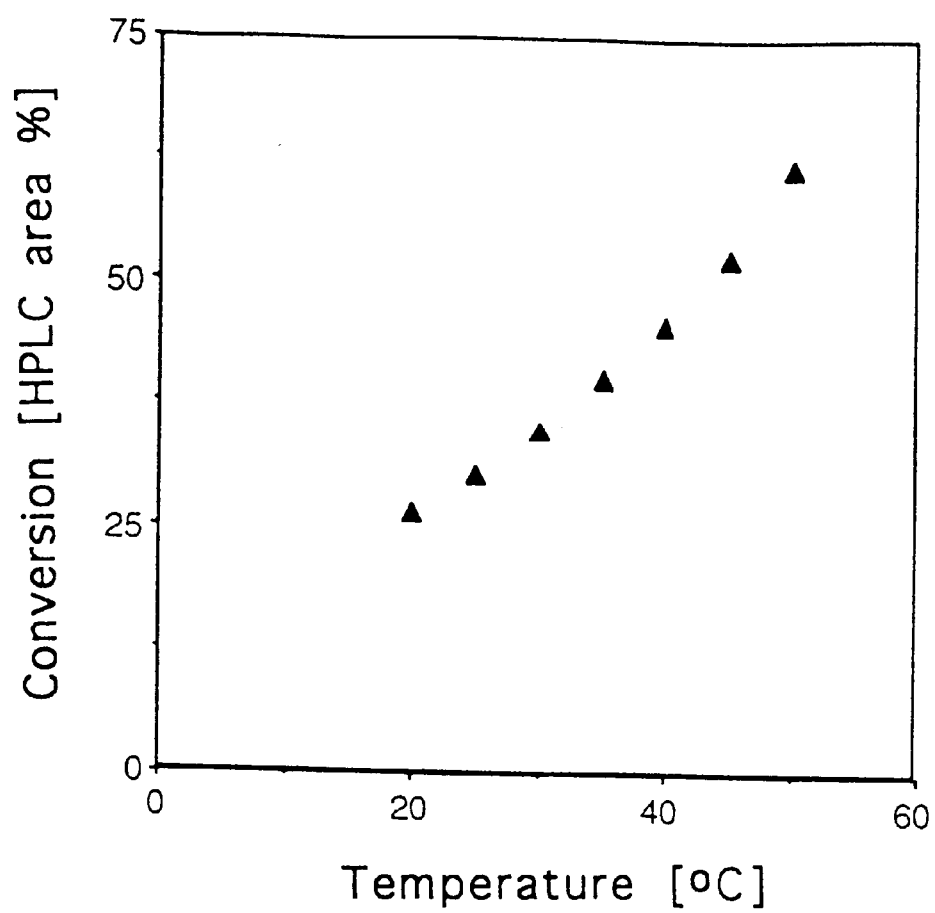
FIG. 3 shows the percent conversion of (11Z,13Z)-7,10-dihydro-10-hydroxy-retinol to B [(11Z,13Z)-7,10-dihydro-10-hydroxy-retinyl acetate] as a function of temperature in a continuous process as provided for in Example 13.

The influence of temperature on the reaction was investigated using a continuous process experiment. 18.0 g (59.1 mmol, 14.4% wt./vol.) of (11Z,13Z)-7,10-dihydro-10-hydroxy-retinol were dissolved in a mixture of 100 ml of toluene, which contained 300 ppm water, and 25 ml of vinyl acetate. The homogeneous mixture was filtered over a membrane filter [RC60, 1 μm, Schleicher & Schuell AG, Dassel, Germany (S&S)] and thereafter pumped with a throughput velocity of 0.5 ml/minute through a column of 10 mm diameter, which had been filled in succession with 7 g of DICALITE® Speedex and 600 mg of lipase PLC (Meito Sangyo). The temperature was varied between 20 and 50°. Reaction samples were removed and analyzed by SFC and HPLC. The results are shown in FIG. 3.

EXAMPLE 14

Figure 4:
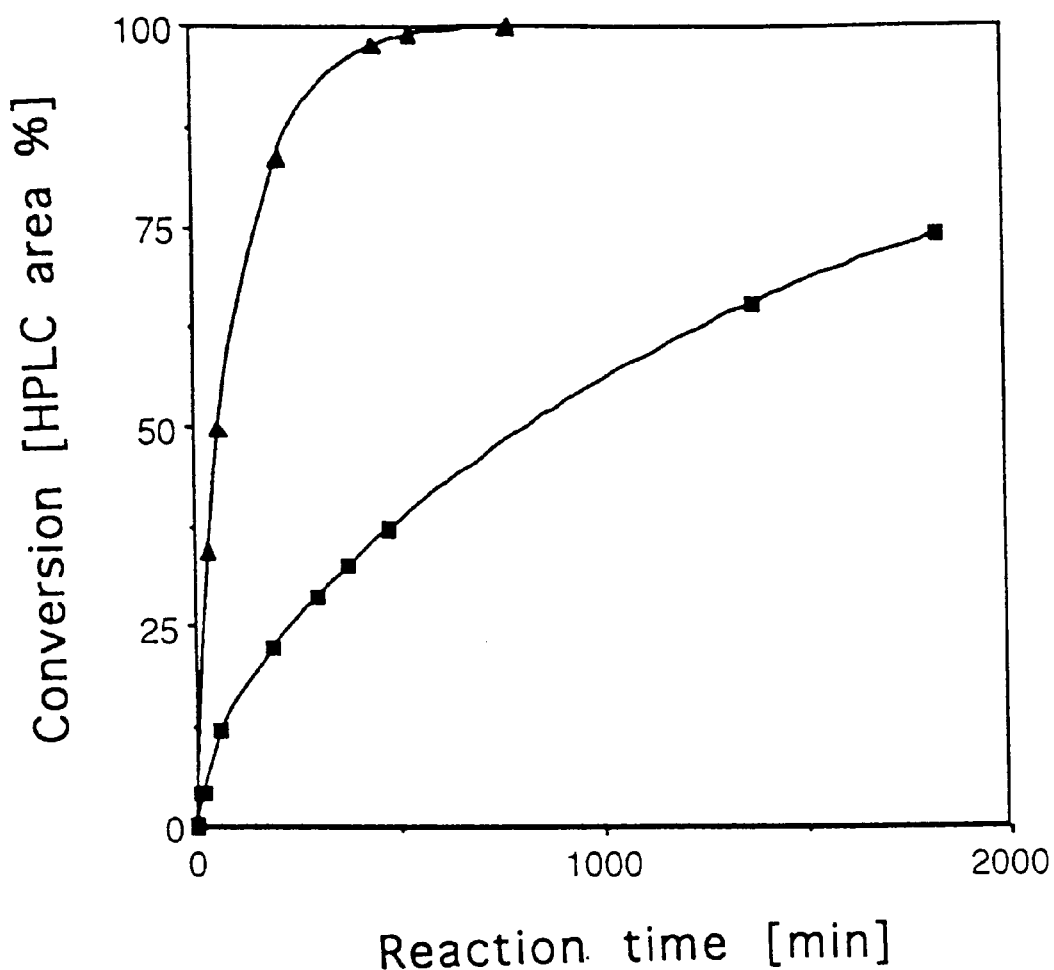
FIG. 4 shows the percent conversion of (11Z,13Z)-7,10-dihydro-10-hydroxy-retinol to B [(11Z,13Z)-7,10-dihydro-10-hydroxy-retinyl acetate] in a batch process with 20% vinyl acetate in toluene at room temperature (■) and with 20% vinyl acetate in toluene at 50° C. ▲ as provided for in Example 14.

The influence of temperature on the reaction was also investigated using a batch process experiment. 48.0 g (157.6 mmol) of (11Z,13Z)-7,10-dihydro-10-hydroxy-retinol were dissolved in sufficient toluene, which contained 20% (wt./vol.) vinyl acetate, such that the resulting mixture had a volume of 240 ml. The homogeneous mixture was then filtered over a membrane filter (RC60, 1 μm, S & S) and held at 50° while stirring (100–110 revolutions/minute). The reaction was started by the addition of 3.0 g of lipase PLC (Meito Sangyo) and followed by HPLC. The results are shown in Table 6 and in FIG. 4.

TABLE 6

| Temperature (° C.) | Reaction time (min.) | Yield (% HPLC) |
| --- | --- | --- |
| Room temp. | 1830 | 73.9 |
| 50 | 780 | 99.9 |

EXAMPLE 15

The influence of solvent on the reaction was investigated using a batch process experiment. 48.0 g (157.6 mmol) of (11Z,13Z)-7,10-dihydro-10-hydroxy-retinol were dissolved in sufficient solvent, which contained 20% (wt./vol.) vinyl acetate, such that the mixture obtained had a volume of 240 ml. The homogeneous mixture was then filtered over a membrane filter (RC60, 1 μm, S & S) and held at 50° while stirring (100–110 revolutions/minute). The reaction was started by the addition of 3.0 g of lipase PLC (Meito Sangyo) and was followed by HPLC. The results are compiled in Table 7:

TABLE 7

| Solvent | Reaction time (min.) | Yield (% HPLC) |
| --- | --- | --- |
| Acetonitrile | 520 | 97.9 |
| Isopropanol | 420 | 57.4 |
| tert.Butanol | 420 | 79.9 |
| Acetone | 1350 | 99.2 |
| Nitromethane | 480 | 97.1 |
| Methylfuran | 395 | 99.5 |
| Tetrahydrofuran | 1380 | 97.0 |
| Triethylamine | 480 | 92.4 |
| Pyridine | 520 | 68.3 |
| Formaldehyde dimethyl acetal | 270 | 99.6 |

TABLE 7-continued

| Solvent | Reaction time (min.) | Yield (% HPLC) |
| --- | --- | --- |
| 1,2-Dimethoxyethane | 480 | 97.3 |
| Diisopropyl ether | 340 | 99.6 |
| Trimethyl orthoformate | 420 | 93.2 |
| tert.Butyl methyl ether | 480 | 99.3 |
| Toluene | 780 | 99.9 |
| 1,4-Dioxan | 1380 | 96.5 |
| Methylene chloride | 340 | 99.5 |
| Chloroform | 480 | 96.7 |
| Hexane | 780 | 99.9 |
| Cyclohexane | 480 | 99.6 |
| Carbon tetrachloride | 480 | 99.3 |

EXAMPLE 16

Figure 5:
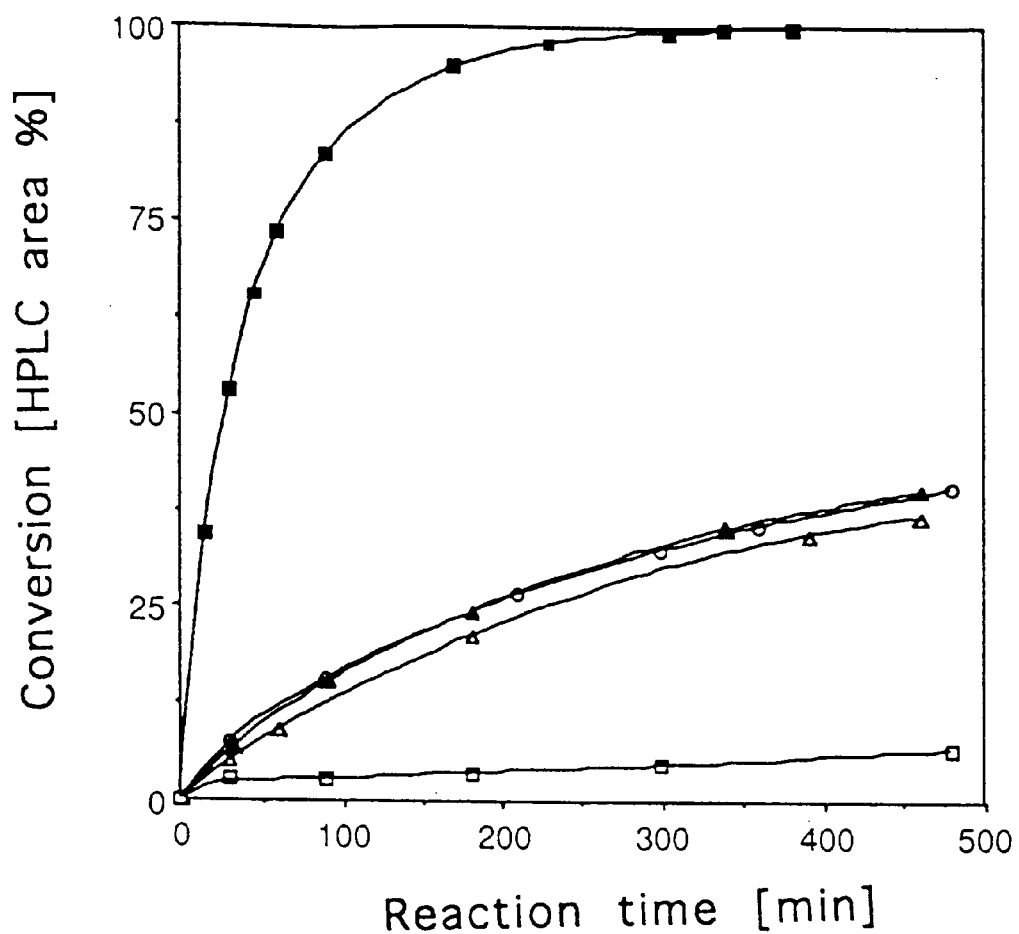
FIG. 5 shows the conversion of (11Z,13Z)-7,10-dihydro-10-hydroxy-retinol to B [(11Z,13Z)-7,10-dihydro-10-hydroxy-retinyl acetate] in a batch process as a function of solvent [vinyl acetate (■); allyl acetate (O); methyl acetate ▲; ethyl acetate (Δ); and isopropenyl acetate (□)] as provided for in Example 16.

The influence of acylating agent on the reaction was investigated using a batch process experiment. 48.0 g (157.6 mmol) of (11Z,13Z)-7,10-dihydro-10-hydroxy-retinol were dissolved in sufficient solvent, which contained 20% (wt./vol.) vinyl acetate, such that the mixture obtained had a volume of 240 ml. The homogeneous mixture was then filtered over a membrane filter (RC60, 1 μm, S & S) and held at 50° while stirring (100–110 revolutions/minute). The reaction was started by the addition of 3.0 g of lipase PLC (Meito Sangyo) and was followed by HPLC. The results are shown in Table 8 and in FIG. 5.

TABLE 8

| Acylating agent | Reaction time (min.) | Yield (% HPLC) |
| --- | --- | --- |
| Vinyl acetate | 340 | 99.5 |
| Methyl acetate | 460 | 40.0 |
| Ethyl acetate | 460 | 36.7 |
| Isopropenyl acetate | 480 | 6.7 |
| Allyl acetate | 480 | 40.2 |

EXAMPLE 17

The influence of the acylating agent on the reaction was investigated using a batch process experiment. 0.5 g (1.64 mmol) of (11Z,13Z)-7,10-dihydro-10-hydroxy-retinol was dissolved or suspended in 5 ml of vinyl ester. The reaction was started by the addition of 12.5 mg of lipase PLC (Meito Sangyo), the mixture was stirred (roller stirrer) at room temperature for 17 hours and the reaction was followed by HPLC. The results are shown in Table 9.

TABLE 9

| Vinyl ester | Yield (% HPLC) |
| --- | --- |
| Vinyl acetate | 87.5 |
| Vinyl propionate | 47.6 |
| Vinyl butyrate | 81.2 |
| Vinyl crotonate | 14.8 |
| Vinyl laurate | 21.6 |

EXAMPLE 18

The influence of the acylating agent on the reaction was investigated using a batch process experiment. 0.5 g (1.64 mmol) of (11Z,13Z)-7,10-dihydro-10-hydroxy-retinol was dissolved or suspended in 5 ml of vinyl ester. The reaction was started by the addition of 12.5 mg of lipase L-2 (Chirazyme® L-2, Boehringer Mannheim GmbH, formerly Novozym® 435 from Novo Nordisk), the mixture was stirred (roller stirrer) at room temperature for 17 hours and the reaction was followed by HPLC. The results are shown in Table 10.

TABLE 10

| Vinyl ester | Yield (% HPLC) |
| --- | --- |
| Vinyl acetate | 96.3 |
| Vinyl propionate | 77.2 |
| Vinyl butyrate | 99.0 |
| Vinyl crotonate | 2.8 |
| Vinyl laurate | 36.3 |

We claim:

1. A process for making a compound of formula

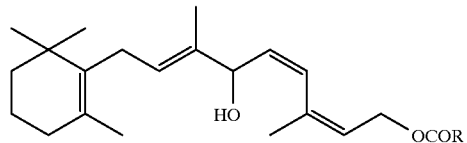

I wherein R signifies a $C_{1-23}$-alkyl group or a $C_{2-23}$-alkenyl group containing 1 to 3 double bonds, comprising the steps of (a) reacting a compound of formula

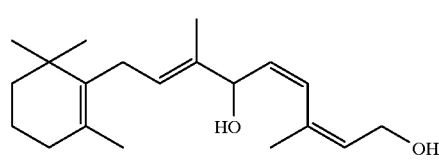

II with an acylating agent which is in a mixture comprising (i) an organic solvent and (ii) a lipase from class EC 3.1.1.3 in suspension in said organic solvent, so as to form the compound of formula I; and (b) recovering the compound of formula I.

2. The process according to claim 1, wherein the lipase is selected from the group consisting of lipase PL from Alcaligenes sp., lipase PLC, lipase PLG, lipase MY-30 from *Candida cylindracea* (*Candida rugosa*), lipase IM-20 from Mucor miehei (*Rhizomucor miehei*), lipase CE-5 from *Humicola lanuginosa*, lipase G from *Penicillium cyclopium*, and lipase L-2 from *Candida antarctica*.

3. The process according to claim 2, wherein the lipase is selected from the group consisting of lipase PL, lipase PLC, lipase PLG, lipase IM-20 and lipase L-2.

4. The process according to claim 3, wherein the lipase is selected from the group consisting of lipase PL, lipase PLC, lipase PLG and lipase L-2.

5. The process according to claim 4, wherein the lipase is lipase L-2.

6. The process according to claim 1, wherein R signifies a $C_{1-23}$-alkyl group.

7. The process according to claim 6, wherein R signifies methyl.

8. The process according to claim 1, wherein the lipase is in immobilized form.

9. The process according to claim 8, wherein the lipase has been immobilized by a cholanic salt selected from the group consisting of sodium cholate and sodium deoxycholate.

10. The process according to claim 1, wherein the reaction of step (a) is further carried out with the exclusion of light.

11. The process according to claim 10, wherein the reaction mixture of step (a) further comprises a radical scavenger.

12. The process according to claim 1, wherein the reaction mixture of step (a) further comprises a radical scavenger.

13. The process according to claim 2, wherein the amount of lipase is from about 0.1 wt % to about 20 wt % based on the amount of compound of formula II.

14. The process according to claim 13, wherein the amount of lipase is from about 0.1 wt % to about 10 wt %.

15. The process according to claim 14, wherein the amount of lipase is from about 1 wt % to about 5 wt %.

16. The process according claim 1, wherein the organic solvent is selected from the group consisting of an aliphatic hydrocarbon of from 5 to 8 carbon atoms, a cyclic hydrocarbon of from 6 to 10 carbon atoms, a chlorinated aliphatic hydrocarbon, a nitro-substituted aliphatic hydrocarbon, an aromatic hydrocarbon, an aliphatic ether, a cyclic ether, an aliphatic ester, an aliphatic ketone, an aliphatic nitrile, an aliphatic amine, an aliphatic acetal and mixtures formed therefrom.

17. The process according to claim 16, wherein the organic solvent is selected from the group consisting of n-hexane, cyclohexane, methylene chloride, carbon tetrachloride, toluene, diisopropyl ether, tetrahydrofuran, methylfuran, vinyl acetate, vinyl propionate, formaldehyde dimethyl acetal, and mixtures formed therefrom.

18. The process according to claim 17, wherein the organic solvent is selected from the group consisting of methylene chloride, diisopropyl ether, tetrahydrofuran, vinyl acetate, vinyl propionate, methylfuran, formaldehyde dimethyl acetal, and mixtures formed therefrom.

19. The process according to claim 1, wherein the acylating agent is selected from the group consisting of alkyl acylates and alkenyl acylates.

20. The process according to claim 19, wherein the acylating agent is an alkyl acylate.

21. The process according to claim 20, wherein the alkyl acylate is selected from the group consisting of methyl acetate, ethyl acetate, butyl acetate, ethyl propionate, and ethyl butyrate.

22. The process according to claim 21, wherein the alkyl acylate is selected from the group consisting of ethyl acetate and butyl acetate.

23. The process according to claim 19, wherein the acylating agent is an alkenyl acylate.

24. The process according to claim 23, wherein the alkenyl acylate is selected from the group consisting of vinyl acetate, allyl acetate, isopropenyl acetate, and vinyl propionate.

25. The process according to claim 24, wherein the alkenyl acylate is vinyl acetate.

26. The process according to claim 1, wherein the concentration of compound of formula II in step (a) is from about 10% (wt/vol) to about 50% (wt/vol).

27. The process according to claim 26, wherein the concentration of compound of formula II is from about 20% (wt/vol) to about 40% (wt/vol).

28. The process according to claim 1, wherein the reaction of step (a) occurs at a temperature of from about 10° C. to about the reflux temperature of the mixture.

29. The process according to claim 28, wherein the reaction of step (a) occurs at a temperature of from about room temperature to about 90° C.

30. The process according to claim 29, wherein the reaction of step (a) occurs at a temperature of from about room temperature to about 60° C.

31. The process according to claim 1, wherein the reaction mixture of step (a) further comprises water, the amount of water being less than 0.2% of the mixture.

32. The process according to claim 1, wherein the reaction mixture of step (a) further comprises a weak base.

33. The process according to claim 32, wherein the weak base is selected from the group consisting of ammonium bicarbonate and ammonium hydroxide.

34. The process according to claim 1, wherein the reaction mixture of step (a) further comprises a weak organic base.

35. The process according to claim 34, wherein the organic base is selected from the group consisting of triethylamine and ethyldiisopropylamine.

36. The process according to claim 1, wherein the reaction of step (a) is carried out as a repeated batch process.

37. The process according to claim 1, wherein the reaction of step (a) is carried out as a continuous process.

* * * * *